US010183089B2

(12) United States Patent
Kitamura

(10) Patent No.: US 10,183,089 B2
(45) Date of Patent: Jan. 22, 2019

(54) MEDICAL INSTRUMENT STERILIZATION METHOD AND STERILIZATION CONTROL DEVICE

(71) Applicant: Terumo Kabushiki Kaisha, Tokyo (JP)

(72) Inventor: Hikaru Kitamura, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 206 days.

(21) Appl. No.: 14/661,549

(22) Filed: Mar. 18, 2015

(65) Prior Publication Data
US 2015/0190541 A1   Jul. 9, 2015

Related U.S. Application Data

(63) Continuation of application No. PCT/JP2013/057396, filed on Mar. 15, 2013.

(51) Int. Cl.
*A61L 2/24* (2006.01)
*A61L 2/07* (2006.01)
(Continued)

(52) U.S. Cl.
CPC ............... *A61L 2/24* (2013.01); *A61L 2/07* (2013.01); *A61L 2/28* (2013.01); *A61L 2202/14* (2013.01);
(Continued)

(58) Field of Classification Search
CPC ................. A61L 2/24; A61L 2/28; A61L 2/07
See application file for complete search history.

(56) References Cited

U.S. PATENT DOCUMENTS 3,093,449 A * 6/1963 Kotarski ................... A61L 2/24
422/112
3,897,818 A * 8/1975 Champel ................... A23L 3/10
165/96
(Continued)

FOREIGN PATENT DOCUMENTS

EP    0 067 420 B1    11/1987
EP    1 287 751 A2    3/2003
(Continued)

OTHER PUBLICATIONS

International Search Report dated Jun. 11, 2013 issued in PCT/JP2013/057396.

*Primary Examiner* — Regina M Yoo
(74) *Attorney, Agent, or Firm* — Foley & Lardner LLP

(57) ABSTRACT

A sterilization method for a medical instrument housed in a housing container includes a temperature-increasing step of housing the housing container in the autoclave and introducing high pressure steam into the autoclave to increase a temperature within the autoclave to a prescribed temperature, a cover sheet being thermally bonded to a peripheral wall portion of the container main body; a sterilizing step of holding the temperature within the autoclave at the prescribed temperature for a prescribed time to sterilize a medical instrument; and a cooling step of reducing the temperature within the autoclave. In the temperature-increasing step, the sterilizing step, and the cooling step, compressed gas is introduced into the autoclave under a steam atmosphere obtained by the introduction of the high pressure steam to increase a current pressure in the autoclave to higher than or equal to a pressure in the housing container and inhibit the cover sheet from peeling from the peripheral wall portion.

14 Claims, 9 Drawing Sheets

(51) Int. Cl.
*A61L 2/28* (2006.01)
*A61M 5/00* (2006.01)

(52) U.S. Cl.
CPC .......... *A61L 2202/24* (2013.01); *A61M 5/002* (2013.01); *A61M 5/008* (2013.01)

(56) References Cited

U.S. PATENT DOCUMENTS

| | | | | |
|---|---|---|---|---|
| 4,092,111 | A * | 5/1978 | Gaignoux | A61L 2/04 422/198 |
| 5,863,499 | A * | 1/1999 | Kralovic | A61L 11/00 206/439 |
| 6,164,044 | A * | 12/2000 | Porfano | B65B 55/10 422/28 |
| 6,189,292 | B1 * | 2/2001 | Odell | B65B 55/10 141/1 |
| 6,250,052 | B1 * | 6/2001 | Porfano | B65B 55/10 53/425 |
| 6,263,641 | B1 * | 7/2001 | Odell | B65B 55/10 53/425 |
| 8,021,445 | B2 * | 9/2011 | Shaffer | C10L 9/08 34/405 |
| 2002/0069616 | A1 * | 6/2002 | Odell | A61M 5/001 53/425 |
| 2002/0192632 | A1 * | 12/2002 | Hei | A61K 35/16 435/2 |
| 2006/0054523 | A1 * | 3/2006 | Porret | A61L 2/08 206/439 |
| 2007/0292305 | A1 * | 12/2007 | Dempsey | A61L 2/206 422/28 |
| 2008/0175752 | A1 * | 7/2008 | Perot | A61L 2/087 422/22 |
| 2009/0081767 | A1 * | 3/2009 | Ogawa | A61L 2/28 435/287.4 |
| 2010/0005710 | A1 * | 1/2010 | Shaffer | C10L 9/08 44/622 |
| 2012/0156096 | A1 * | 6/2012 | Allen | A61L 2/26 422/38 |
| 2014/0093422 | A1 | 4/2014 | Meier et al. | |

FOREIGN PATENT DOCUMENTS

| | | |
|---|---|---|
| JP | 2000-051323 A | 2/2000 |
| JP | 2005-162249 A | 6/2005 |
| JP | 2009-183768 A | 8/2009 |
| JP | 2012-71046 A | 4/2012 |
| WO | WO-1999/045984 A1 | 9/1999 |
| WO | WO-2012/136313 A2 | 10/2012 |

* cited by examiner

REGION A

REGION B

MEDICAL INSTRUMENT STERILIZATION METHOD AND STERILIZATION CONTROL DEVICE

CROSS-REFERENCE TO RELATED APPLICATIONS

This application is a continuation application filed under 35 U.S.C. 111(a) claiming the benefit under 35 U.S.C. §§ 120 and 365(c) of PCT International Application No. PCT/JP2013/057396 filed Mar. 15, 2013, the entire contents of which is hereby incorporated by reference in its entirety.

BACKGROUND

Technical Field

The present disclosure relates to a sterilization method for medical instruments that involves housing a housing container in an autoclave and sterilizing with a high pressure steam, the housing container having a gas permeable and micro-particle impermeable cover sheet thermally bonded and sealed to an opening edge of a container main body housing a medical instrument. The present disclosure also relates to a sterilization control device used in the method.

Background Art

A syringe barrel such as a pre-Tillable syringe, a pre-filled syringe in which the pre-Tillable syringe is filled with drugs such as a medical solution, a medicinal drug such as an infusion solution, a blood bag, and a medical instrument such as a medical device including a catheter need to be in a clean aseptic state until use, and thus, are housed in a resin housing container and sterilized in advance with a process such as a high pressure steam sterilization process in an autoclave. In JP 2009-183768 A, a syringe barrel, attached with a cap for covering a needle at the distal end and housed in a housing container, to be filled with a medical agent is transported to a factory the syringe barrel is filled with the medical agent. JP 2009-183768 describes sealing the opening of the housing container, in which a plurality of empty syringe barrels is housed, by thermally sealing a cover sheet made from a material having gas permeability such as a high density polyethylene unwoven cloth to the opening edge. Sterilization utilizing an autoclave sterilizer is then performed on the housing container.

After removing the cover sheet sealing the opening from the housing container taken out from the autoclave sterilizer in the factory at the transporting destination, each syringe barrel is filled with the medical agent, and a pusher is inserted into each syringe barrel to obtain a pre-filled syringe. The manufactured pre-filled syringe is packaged with a sterilization packaging bag and then transported to a doctor or the like.

The syringe barrel housed in the housing container and sterilized can be transported to the factory at the transporting destination while maintaining such state. The cover sheet sealing the opening of the housing container is thermally bonded to the opening edge of the housing container by way of a heat seal adhesive consisting of thermoplastic resin applied on the back surface thereof so as to be easily removed in the factory at the transporting destination. However, it was revealed that a part of the cover sheet peels from the opening edge of the housing container in the housing container subjected to sterilization with the autoclave sterilizer. The cause was found to be the cover sheet bulging out toward the outer side of the housing container to a projecting state to the extent that the cover sheet is peeled from the opening edge of the housing container during a temperature-increasing step in which the temperature in the autoclave is increased, a sterilizing step, and a cooling step in which the temperature in the autoclave is lowered.

SUMMARY OF INVENTION

In light of the foregoing, one objective of certain embodiments of the present invention is to provide a sterilization method for medical instruments and a sterilization control device that can prevent the peeling of the cover sheet that occurs when the cover sheet bulges out toward the outer side of the container main body to a projecting state during the temperature-increasing step, the sterilizing step, and the cooling step when the housing container is housed in the autoclave and sterilized by high pressure steam, the housing container having the gas permeable and micro-particle impermeable cover sheet thermally bonded and sealed with a heat seal thermoplastic resin to the opening edge of the container main body housing the medical instrument.

According to one embodiment, a sterilization method is provided for a medical instrument housed in a housing container that includes a container main body including a bottom portion at a lower end, a peripheral wall portion extending from a periphery of the bottom portion toward an upper end, and an opening surrounded by the upper end of the peripheral wall portion; and a gas permeable and micro-particle impermeable cover sheet that covers and seals the opening, the cover sheet being thermally bonded to the upper end of the peripheral wall portion of the container main body with a heat seal thermoplastic resin to seal the opening. The method includes a temperature-increasing step of housing the housing container in the autoclave and introducing high pressure steam into the autoclave to increase a temperature within the autoclave to a prescribed temperature; a sterilizing step of holding the temperature within the autoclave at the prescribed temperature for a prescribed time to sterilize the medical instrument; and a cooling step of reducing the temperature within the autoclave. In the temperature-increasing step, the sterilizing step, and the cooling step, compressed gas is introduced into the autoclave under a steam atmosphere obtained by the introduction of the high pressure steam to increase a current pressure in the autoclave to higher than or equal to a pressure in the housing container and inhibit the cover sheet from peeling from the upper end of the peripheral wall portion.

In one aspect, in the temperature-increasing step, when the current pressure becomes lower than a temperature-increasing pressure, which is a pressure obtained by adding a first preset pressure value to a saturated steam pressure corresponding to a current temperature in the autoclave, the compressed gas is introduced to increase the current pressure to higher than or equal to the temperature-increasing pressure. In the sterilizing step, when the current pressure becomes lower than a sterilizing pressure, which is a pressure obtained by adding a second preset pressure value to a saturated steam pressure corresponding to a current temperature in the autoclave, the compressed gas is introduced to increase the current pressure to higher than or equal to the sterilizing pressure.

In one aspect, in the temperature-increasing step, a current temperature and the current pressure in the autoclave are actually measured at every prescribed time, and when the actually measured current pressure becomes lower than a temperature-increasing pressure, which is a pressure obtained by adding a first preset pressure value to a saturated steam pressure corresponding to the actually measured current temperature, the compressed gas is introduced into the autoclave to increase the current pressure to higher than or equal to the temperature-increasing pressure. In the sterilizing step, a current temperature and the current pressure in the autoclave are actually measured at every prescribed time, and when the actually measured current pressure becomes lower than a sterilizing pressure, which is a pressure obtained by adding a second preset pressure value to a saturated steam pressure corresponding to the actually measured current temperature, the compressed gas is introduced into the autoclave to increase the current pressure to higher than or equal to the sterilizing pressure.

In one aspect, the current temperature is actually measured with a temperature sensor arranged near a bottom portion in the autoclave, and each of the first preset pressure value and the second preset pressure value is in a range of 20 to 90 kPa.

In one aspect, in the cooling step, when the current pressure becomes lower than a prescribed pressure that is preset to a pressure higher than the sterilizing pressure, the compressed gas is introduced to increase the current pressure to higher than or equal to the prescribed pressure.

In one aspect, in the temperature-increasing step, the high pressure steam is intermittently introduced into the autoclave.

In one aspect, the method further includes a pressure-reducing step of reducing a pressure of an interior of the autoclave to smaller than an atmosphere pressure before the temperature-increasing step, wherein a pressure-reducing speed in the autoclave in the pressure-reducing step is adjusted to be within a range of 5 to 40 kPa/min In one aspect, in the cooling step, when a current temperature in the autoclave becomes lower than or equal to 60° C., the cooling step is terminated, and a remaining pressure in the autoclave is released to an outside atmosphere such that an interior of the autoclave is at an atmosphere pressure In one aspect, the medical instrument is a syringe barrel configured to be filled with a drug and including a needle at a distal end, a cap that covers the needle, and a flange at a proximal end.

In one aspect, the medical instrument is a syringe barrel configured to be filled with a drug and including a needle at a distal end, a cap that covers the needle, and a flange at a proximal end. The housing container further includes a shelf arranged on the peripheral wall portion and a nested plate that is arranged on the shelf and which a plurality of tubular receiving cylinders penetrates and is arranged on, the tubular receiving cylinders penetrating through the nested plate. Each tubular receiving cylinder is configured such that a syringe barrel is removably insertable therein and hangable thereon by the flange of the syringe barrel.

According to another embodiment, a sterilization control device includes an autoclave configured to house a housing container that includes a container main body having a bottom portion at a lower end, a peripheral wall portion extending from a periphery of the bottom portion toward an upper end of the peripheral wall portion, and an opening surrounded by the upper end of the peripheral wall portion, a medical instrument housed in the container main body, and a gas permeable and micro-particle impermeable cover sheet that covers and seals the opening, the cover sheet being thermally bonded to the upper end of the peripheral wall portion with a heat seal thermoplastic resin to seal the opening; a steam introducing control valve configured to continuously or intermittently introduce a high pressure steam and increase a temperature within the autoclave to a prescribed temperature to sterilize the medical instrument; a temperature sensor configured to measure the temperature in the autoclave; a pressure sensor configured to measure the pressure in the autoclave; a gas introducing control valve configured to introduce compressed gas into the autoclave; a pressure control unit configured to control the gas introducing control valve to introduce compressed gas into the autoclave under a steam atmosphere obtained by the high pressure steam introduced through the steam introducing control valve so that a current pressure within the autoclave measured with the pressure sensor is increased to be higher than or equal to a pressure in the housing container to prevent the cover sheet from peeling from the upper end of the peripheral wall portion; and a sterilization program programmed with a temperature-increasing step of introducing the high pressure steam into the autoclave to increase the temperature within the autoclave to a prescribed temperature, a sterilizing step of holding the temperature within the autoclave at the prescribed temperature for a prescribed time to sterilize the medical instrument, and a cooling step of reducing the temperature within the autoclave.

In one aspect, the pressure control unit includes a comparing device configured to compare a comparative pressure, which is a pressure obtained by adding a preset pressure value to a saturated steam pressure corresponding to the current temperature in the autoclave measured with the temperature sensor for every prescribed time, and the current pressure within the autoclave measured with the pressure sensor in at least the temperature-increasing step and the sterilizing step, and a pressure adjusting device that opens the gas introducing control valve to introduce the compressed gas into the autoclave when the current pressure is lower than the comparative pressure in the comparing device to increase the current pressure to higher than or equal to the comparative pressure.

In one aspect, the temperature sensor is located near the bottom portion of the autoclave. The preset pressure value is in a range of 20 to 90 kPa.

According to certain embodiments of the present invention, even when the housing container is housed in the autoclave and sterilized with high pressure steam, the housing container having a gas permeable and micro-particle impermeable cover sheet thermally bonded to an opening edge of a container main body housing a medical instrument with a heat seal thermoplastic resin, the cover sheet can be prevented from bulging out toward the outer side of the container main body to a projecting state to the extent that the cover sheet is peeled from the opening edge of the container main body during the temperature increasing step, the sterilizing step, and the cooling step. As a result, the cover sheet is prevented from peeling from the container main body during the temperature-increasing step, the sterilizing step, and the cooling step. Thus, the reliability of the sterilized medical instrument can be enhanced, and the housing container taken out from the autoclave can be transported with the usual transporting means as is. Because the cover sheet is thermally bonded to the container main body with the heat seal thermoplastic resin, the cover sheet can be easily peeled after sterilization, and the removing operability of the cover sheet can also be enhanced.

DETAILED DESCRIPTION

Modes for implementing the present invention will be described in detail below, but the scope of the present invention is not to be limited to such modes.

Figure 1:
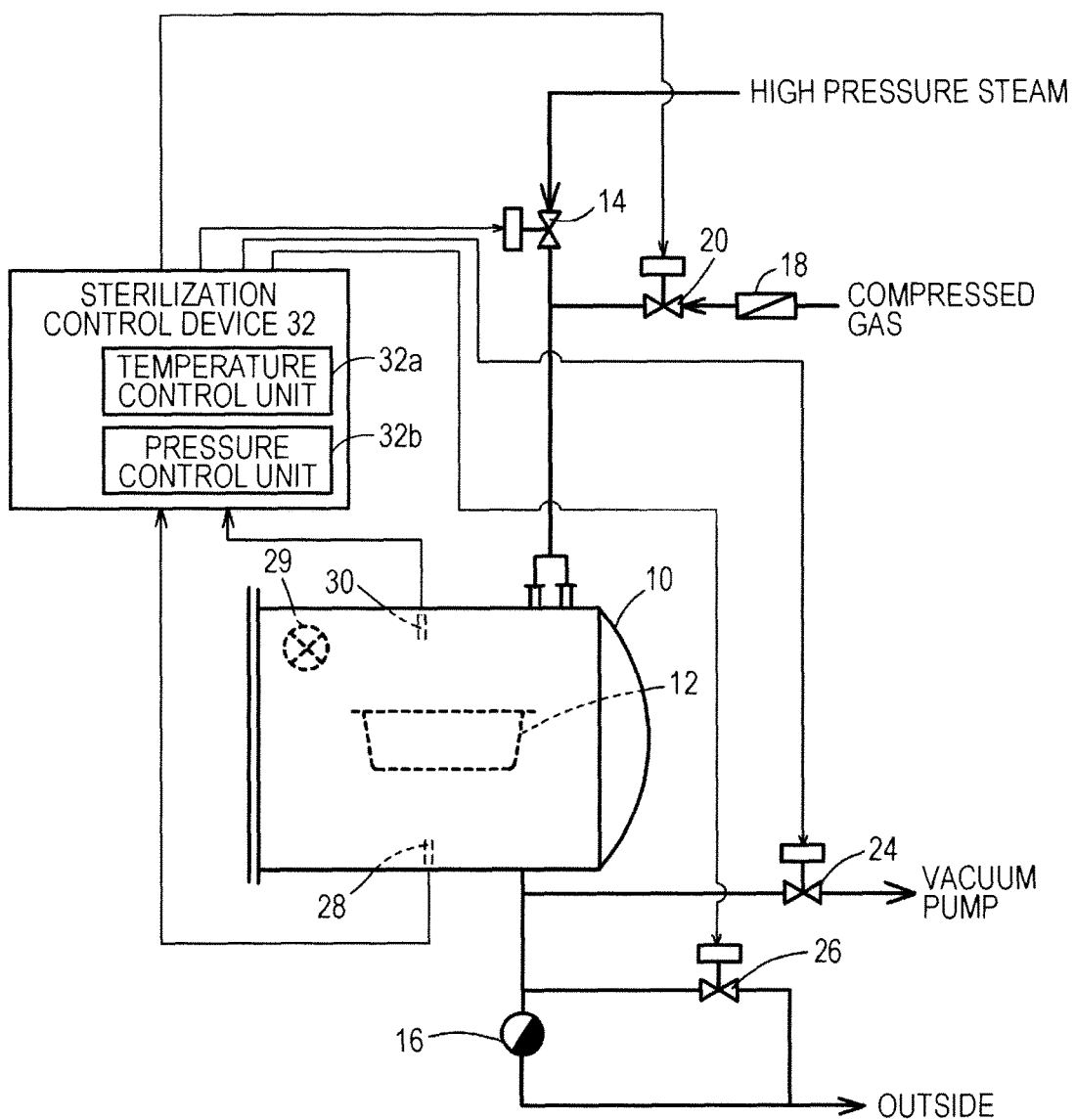
FIG. 1 is a schematic view showing one example of a sterilizing device to apply a sterilization method for medical instruments according to one embodiment of the present invention.
Figure 2A:
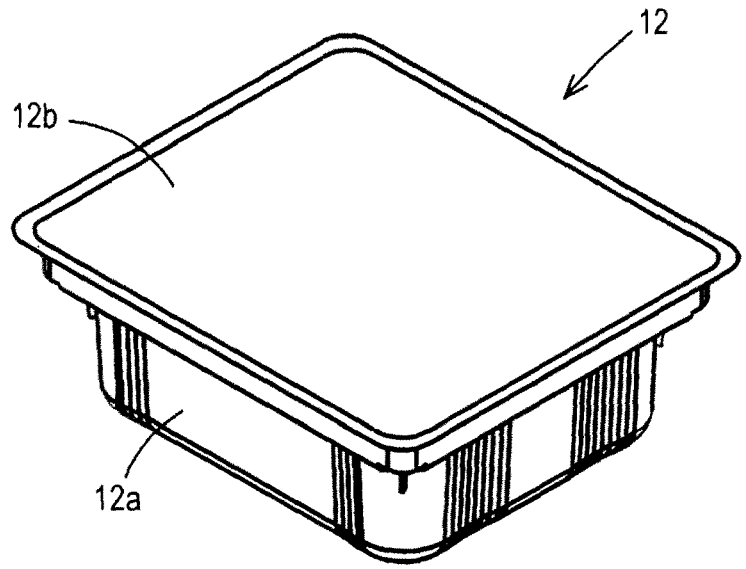
FIG. 2(A) is a perspective view of a housing container housing a medical instrument.
Figure 2B:
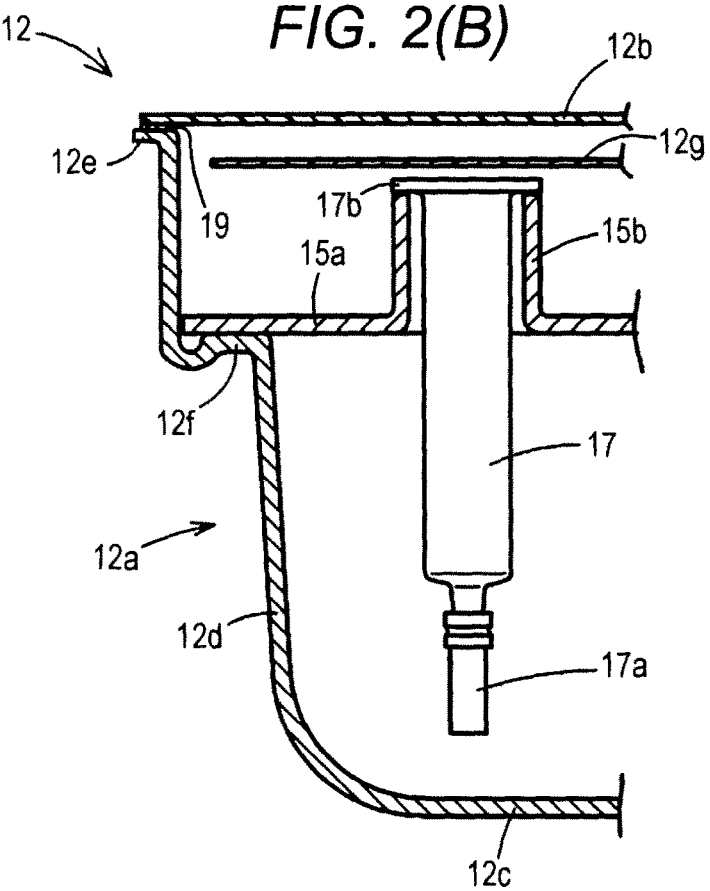
FIG. 2(B) is a partial cross-sectional view of a housing container housing a medical instrument.

One example of a sterilizing device to apply a sterilization method for medical instruments according to one embodiment of the present invention is shown in FIG. 1. A housing container 12 housing an empty syringe barrel, serving as an example of a medical instrument, is housed in an autoclave 10 shown in FIG. 1. The housing container 12 has an opening of a container main body 12a sealed with a gas permeable and micro-particle impermeable cover sheet 12b, as shown in FIG. 2(A). As shown in FIG. 2(B), the housing container 12 includes: a container main body 12a having a bottom portion 12c at a lower end, a peripheral wall portion 12d that continues to the periphery of the bottom portion 12c and extends toward an upper end, an opening surrounded by an upper end 12e of the peripheral wall portion 12d, and a shelf 12f provided on the peripheral wall portion 12d; and a nested plate 15a placed on the shelf 12f and having tubular receiving cylinders 15b penetrating and being arranged on the nested plate 15a. As shown in FIG. 2(B), a syringe barrel 17 to be filled with drugs including a needle (not shown) at a distal end, a cap 17a for covering the needle, and a flange 17b at a proximal end is inserted into the receiving cylinder 15b in a freely insertable/removable manner as a medical instrument. The flange 17b is engaged at a distal end face of the receiving cylinder 15b to suspend the syringe barrel 17. The material of the container main body 12a, and nested plate 15a including the receiving cylinder 15b may be plastic, for example, polyolefin resin such as polyethylene, polypropylene, and annular polyolefin; polystyrene; polycarbonate; polyester such as polyethylene terephthalate; and polyamide. In particular, the use of polypropylene, polycarbonate, or the like, which is a plastic having high heat resistance, is preferred. Either glass or the above-described plastic can be used for the material of the syringe barrel 17. The plastic used for the syringe barrel 17 is preferably an annular olefin homopolymer or annular olefin copolymer, which is a plastic that is transparent so that the medical solution filled inside can be visually checked from the outside and in which interaction with the medical solution is small.

An inner sheet 12g covering the proximal end opening of the syringe barrel 17 is placed on the flange 17b of the syringe barrel 17 suspended from the nested plate 15a. The shape of the inner sheet 12g is a substantially rectangular shape greater than the shelf 12f and smaller than the opening of the container main body 12a. The inner sheet 12g prevents foreign substances such as dust that dropped from above from attaching to the syringe barrel 17, in particular, the interior of the syringe barrel 17 when the cover sheet 12b sealing the opening of the container main body 12a is peeled. A plastic film or an unwoven cloth similar to the cover sheet 12b, to be described later, is preferably used for the material of the inner sheet. When peeling the cover sheet 12b from the housing container 12 in a clean room, for example, the inner sheet 12g may be omitted.

The cover sheet 12b sealing the opening of the container main body 12a allows permeation of gas such as steam, but does not allow permeation of micro-particles such as micro-organisms, floating dusts, and the like. The cover sheet 12b is preferably an unwoven cloth, and an unwoven cloth thermally compression bonded with a continuous ultrafine fiber consisting of high density polyethylene resin and having a thickness of 0.5 to 10 μm, for example, TYVEK (registered trademark) manufactured from Du Pont Co., can be suitably used. The cover sheet 12b has a heat seal thermoplastic resin 19 applied to a surface (back surface) facing the opening of the container main body 12a, and the cover sheet 12b is thermally bonded to the upper end 12e of the peripheral wall portion 12d, which is the opening edge of the container main body 12a, with the heat seal thermoplastic resin 19, as shown in FIG. 2(B). The heat seal thermoplastic resin 19 is provided to be heated and seal the cover sheet 12b and the upper end 12e of the container main body 12a in a peelable manner. The temperature for heating and sealing is preferably lower than or equal to 150° C. Specifically, if the container main body 12a is made of polypropylene, then ethylene-vinyl acetate resin, ethylene-acrylate resin, olefin resin in which polypropylene and polyethylene are blended, and the like can be used for the heat seal thermoplastic resin 19.

The heat seal thermoplastic resin 19 is preferably not applied to at least a region facing the upper surface of the medical instrument (flange 17b of syringe barrel 17) housed in the housing container 12, and in particular, is preferably not applied to a region facing the inner sheet 12g. Thus, even when the cover sheet 12b is recessed toward the inner side of the container main body 12a to a recessed state by the control of a pressure control unit 32b, to be described later, the cover sheet 12b can be prevented from attaching to the inner sheet 12g or the upper surface of the medical instrument (flange 17b of syringe barrel 17) by the softened heat seal thermoplastic resin 19.

The housing container 12 in which an opening of the container main body 12a, where each of the plurality of syringe barrels 17 is housed by being suspended from the receiving cylinder 15b for the medical instrument, is sealed with the cover sheet 12b and is housed in the autoclave 10 shown in FIG. 1. A high pressure steam is introduced into the autoclave 10 via a high pressure steam introducing control valve 14, and the interior of the autoclave 10 is held for a prescribed time at a prescribed temperature and a prescribed pressure. Meanwhile, the steam in the autoclave 10 passes through the gas permeable and micro-particle impermeable cover sheet 12b to enter the housing container 12, thus performing the sterilization process on the syringe barrel 17.

The steam in the autoclave 10 increases the temperature of each of the autoclave 10 and the housing container 12 and then condenses to become a drain. The generated drain is discharged to the outside via a drain trap 16 arranged on the bottom surface side of the autoclave 10. Furthermore, a compressed gas that is passed through a filter 18 and cleaned can be introduced into the autoclave 10 via a gas introducing control valve 20. The inner pressure of the autoclave 10 that became a higher pressure than an atmosphere pressure by introducing the high pressure steam and the compressed gas can have its pressure reduced to the atmosphere pressure by opening a release control valve 26 and discharging the steam and the compressed gas in the autoclave 10 to the atmosphere outside. In reducing the pressure, the opening degree of the release control valve 26 is adjusted, and the pressure-reducing speed in the autoclave 10 is preferably adjusted to about 5 to 40 kPa/min. The autoclave 10 can be coupled to a vacuum pump (not shown) by way of a pressure-reducing control valve 24 arranged on the bottom surface side to reduce the pressure of the interior of the autoclave 10 to lower than or equal to the atmosphere pressure.

A temperature sensor 28 for measuring the inner temperature and a pressure sensor 30 for measuring the inner pressure are arranged in the autoclave 10, and the data signals thereof are transmitted to the sterilization control device 32. A temperature control unit 32a and the pressure control unit 32b of the sterilization control device 32 transmit a signal to the high pressure steam introducing control valve 14, the gas introducing control valve 20, the pressure-reducing control valve 24, and the release control valve 26 in a predefined order and open/close each control valve to proceed a prescribed step. The time in which the high pressure steam introducing control valve 14 and the gas introducing control valve 20 are opened is set in advance in the temperature control unit 32a and the pressure control unit 32b.

The temperature sensor 28 for measuring the inner temperature and the pressure sensor 30 for measuring the inner pressure are arranged in the autoclave 10, and the data signals thereof are transmitted to the sterilization control device 32. The temperature control unit 32a and the pressure control unit 32b of the sterilization control device 32 transmit a signal to the high pressure steam introducing control valve 14, the gas introducing control valve 20, the pressure-reducing control valve 24, and the release control valve 26 in a predefined order and open/close each control valve to proceed a prescribed step. The time in which the high pressure steam introducing control valve 14 and the gas introducing control valve 20 are opened is set in advance in the temperature control unit 32a and the pressure control unit 32b.

Since the temperature near the bottom portion tends to become lower than the temperature near the upper portion in the autoclave 10, the temperature sensor is preferably arranged near the bottom portion of the autoclave 10. Thus, the entire interior of the autoclave 10 can be reliably maintained at higher than or equal to a sterilizing temperature in the sterilizing step, to be described later. Furthermore, a fan 29 is arranged in the autoclave 10. The gas in the autoclave 10 is stirred with the fan 29 to reduce the temperature variation in the autoclave.

The sterilization method for medical instruments using the sterilization control device 32 will be described in detail below. The temperature control unit 32a of the sterilization control device 32 shown in FIG. 1 controls sterilization the syringe barrel 17 housed in the housing container 12 in the autoclave 10 according to the procedure shown in the flowchart of FIG. 3. First, when the switch of the sterilizing device is turned ON, the pressure-reducing step is started in step S10. In step S10, the vacuum pump is driven, and the pressure-reducing control valve 24 is opened so that the interior of the autoclave 10 is in the pressure-reduced state lower than or equal to the atmosphere pressure. In this case, the opening degree of the pressure-reducing control valve 24 is adjusted, and the pressure-reducing speed in the autoclave 10 is preferably adjusted to about 5 to 40 kPa/min. When the pressure-reducing speed becomes greater than 40 kPa/min., the inner pressure of the autoclave 10 drastically becomes lower than the inner pressure of the housing container 12, and the cover sheet 12b may bulge out and peel off. When the pressure-reducing speed is lower than 5 kPa/min., the cover sheet 12b does not bulge out to an extent of peeling, but the time in the pressure-reducing step tends to become long. After the pressure-reducing step is started, the current pressure measured with the pressure sensor 30 and the set pressure set in advance, for example, 10 kPa, are compared in step S12, where the pressure-reducing step is continued if the current pressure is higher than the set pressure. If the current pressure is lower than or equal to the set pressure, the vacuum pump is stopped in step S14, the pressure-reducing control valve 24 is closed, and the pressure-reducing step is terminated. After introducing the high pressure steam into the autoclave 10 in the pressure-reduced state until returning to approximately the atmosphere pressure, as necessary, the pressure-reducing step is again carried out and is repeated as desired to replace the interior of the autoclave 10 with a steam atmosphere.

The temperature-increasing step is started in step S16. The temperature-increasing step is the step of introducing the high pressure steam into the autoclave 10 in the pressure-reduced state and increasing the inner temperature of the autoclave 10 including the syringe barrel 17 housed in the housing container 12 up to the sterilizing temperature. In step S20, the high pressure steam introducing control valve 14 is opened to introduce the high pressure steam into the autoclave 10, and the counting of the introducing time set in advance is started. If the introducing time has not elapsed in step S22, the high pressure steam is continued to be introduced. If the introducing time has elapsed in step S22, the counting of the introducing time is reset, and the high pressure steam introducing control valve 14 is closed to stop the introduction of the high pressure steam in step S24. In this case, the counting of a waiting time A of the introduction of the high pressure steam set in advance is started. If the waiting time A has elapsed in step S25, the process proceeds to step S26 and the counting of the waiting time A is reset. The current temperature measured with the temperature sensor 28 and the sterilizing temperature set in advance are compared in step S26, where if the current temperature is lower than the sterilizing temperature, the process returns to step S20, and the high pressure steam introducing control valve 14 is opened to introduce the high pressure steam into the autoclave 10 until elapse of the introducing time. If the current temperature is higher than or equal to the sterilizing temperature in step S26, the temperature-increasing step is terminated in step S28. The sterilizing temperature is preferably set to 121 to 125° C. The waiting time A and the introducing time are preferably set to five to ten seconds. Thus, the temperature variation in the autoclave 10 in the temperature-increasing step can be reduced, and the entire interior of the autoclave 10 can be reliably made to be higher than or equal to the sterilizing temperature in the sterilizing step, to be described later.

After the temperature-increasing step is terminated in step S28, the sterilizing step is started in step S30. In this case, the counting of the sterilizing time set in advance is started. The sterilizing time is preferably set to about 20 to 60 minutes. Furthermore, in step S32, the current temperature measured with the temperature sensor 28 and the sterilizing temperature set in advance are compared, and whether the current temperature in the autoclave 10 is maintained at higher than or equal to the sterilizing temperature set in advance is monitored. The sterilizing temperature is preferably set to 121 to 125° C. If the current temperature in the autoclave 10 is maintained at higher than or equal to the sterilizing temperature, whether the sterilizing time set in advance has elapsed is determined in step S34. If the sterilizing time has not elapsed, the process returns to step S32. If the sterilizing time has elapsed in step S34, the process proceeds to step S36 and the sterilizing step is terminated. The counting of the sterilizing time is then reset.

If the current temperature measured with the temperature sensor 28 is lower than the sterilizing temperature set in advance due to heat release from the autoclave 10 and the like in step S32, the process proceeds to step S50. In step S50, the necessary introducing time of the high pressure steam necessary to have the current temperature in the autoclave 10 higher than or equal to the sterilizing temperature is calculated and set. Then, the process proceeds to step S52, whether the high pressure steam introducing control valve 14 is opened to start the introduction of the high pressure steam, and the counting of the necessary introducing time is started. Furthermore, whether the necessary introducing time has elapsed is determined in step S54, and the introduction of the high pressure steam is continued if the necessary introducing time has not elapsed. If the necessary introducing time has elapsed in step S54, the high pressure steam introducing control valve 14 is closed to stop the introduction of the high pressure steam in step S56, and the process returns to step 32 to determine whether the current temperature measured with the temperature sensor 28 is higher than or equal to the sterilizing temperature set in advance. If the current temperature in the autoclave 10 is maintained at higher than or equal to the sterilizing temperature set in advance, the process proceeds to step 34, and whether or not the sterilizing time has elapsed is determined. The necessary introducing time of the high pressure steam is about one to five seconds.

The autoclave 10, in which the sterilizing step is terminated in step S36, then enters a cooling step of being cooled to the inner temperature at which the housed housing container 12 can be taken out in step S38. In the cooling step, the inner temperature of the autoclave 10 is lowered by heat release from the autoclave 10 itself. In this case, the drain generated by the condensation of the steam in the autoclave 10 is discharged to the outside from the drain trap 16. With respect to the inner temperature of the autoclave 10, whether the current temperature (inner temperature) measured with the temperature sensor 28 is lower than or equal to the cooling temperature set in advance is determined in step S40. The cooling step is continued if the current temperature is higher than the cooling temperature, whereas the process proceeds to step S42 to terminate the cooling step if the current temperature is lower than or equal to the cooling temperature, and a series of steps is terminated. For example, the cooling temperature may be 30 to 60° C. In step S42, when the cooling step is terminated, the release control valve 26 is released to release the remaining pressure in the autoclave 10 to the atmosphere outside to have the interior of the autoclave 10 at the atmosphere pressure. When releasing the remaining pressure, the pressure-reducing speed in the autoclave 10 is preferably adjusted with the release control valve 26 to become 5 to 40 kPa/min. to prevent the cover sheet 12*b* from peeling from the container main body 12*a*. At the time of pressure-reduction, the current temperature in the autoclave 10 is 30 to 60° C. (preferably 40 to 50° C.). Thus, the heat seal thermoplastic resin 19 is sufficiently solidified, whereby the peeling of the cover sheet 12*b* from the container main body 12*a* can be prevented. The housed housing container 12 can then be taken out from the autoclave 10, whereby the cooling step is terminated.

Figure 3:
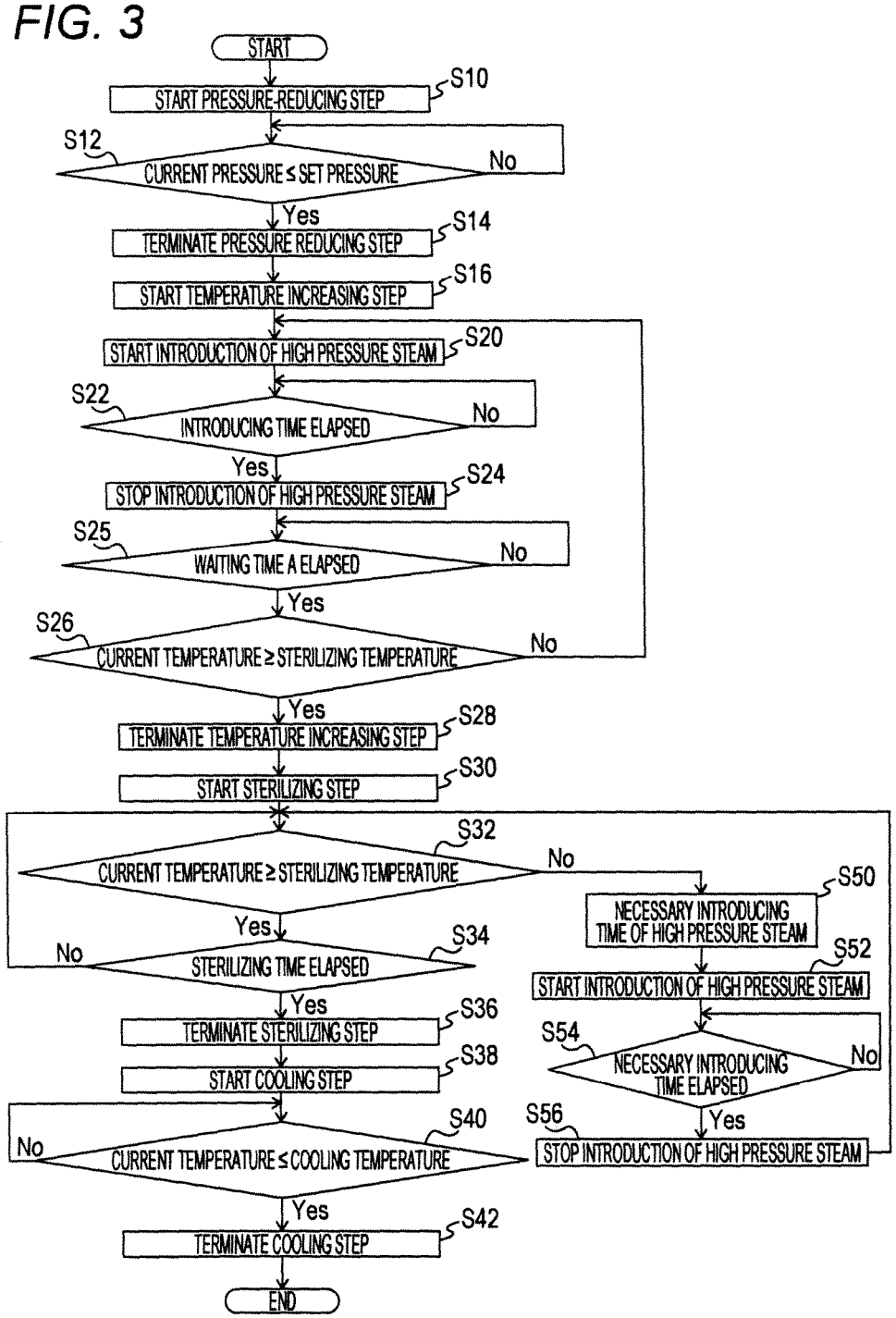
FIG. 3 is a flowchart of a temperature control unit of the sterilizing device shown in FIG. 1.

If only the high pressure steam is introduced into the autoclave 10 by the temperature control unit 32*a*, as shown in the flowchart of FIG. 3, the cover sheet 12*b* may bulge out toward the outer side of the housing container 12 to a projecting state in the temperature-increasing step, the sterilizing step, and the cooling step. This will be described with a graph, shown in FIG. 4, that shows the temporal change of the pressure and the temperature in the temperature-increasing step. In the temperature-increasing step of the flowchart shown in FIG. 3, the high pressure steam is intermittently introduced into the autoclave 10. When the introduction of the high pressure steam to the autoclave 10 is started, the inner pressure of the autoclave 10 immediately rises, but the inner pressure in the housing container 12, into which the steam enters from the cover sheet 12*b*, starts to rise later than the rise of the inner pressure of the autoclave 10. Thus, the inner pressure of the housing container 12 is lower than the inner pressure of the autoclave 10. After the introduction of the high pressure steam is stopped, the steam in the autoclave 10 is heat exchanged with the autoclave 10 main body, the housing container 12, and the like, and then the steam is cooled and condensed to become the drain, causing the inner pressure in the autoclave 10 to immediately lower. When the introduction of the high pressure steam is stopped, the inner pressure of the housing container 12 rises by the plastic container main body 12*a* being warmed by the heat exchange with the steam and by the steam that enters by pressure gradient, but the inner pressure in the autoclave 10 is still higher than the inner pressure of the housing container 12. Thus, in a region A where the inner pressure in the autoclave 10 is higher than the inner pressure of the housing container 12, the cover sheet 12*b* recesses toward the inner side of the container main body 12*a* to the recessed state, and the force caused in this recessed state acts in the direction of pushing the cover sheet 12*b* with respect to the heat seal thermoplastic resin 19.

The inner pressure of the housing container 12 also starts to lower after the start of lowering of the inner pressure in the autoclave 10, and the plastic housing container 12 is difficult to cool compared to the autoclave 10 made of metal, and thus the steam in the housing container 12 is less likely to be condensed, and the lowering speed of the inner pressure of the housing container 12 becomes slower than the lowering speed of the inner pressure in the autoclave 10. Thus, a region B where the inner pressure of the housing container 12 becomes higher than or equal to the inner pressure of the autoclave 10 is generated. In the region B, the cover sheet 12*b* bulges out toward the outer side of the container main body 12*a* to a projecting state, and a force acts in the direction of peeling the cover sheet 12*b* with respect to the heat seal thermoplastic resin 19. In the temperature-increasing step shown in FIG. 4, the region A, in which the cover sheet 12b is recessed toward the inner side of the container main body 12a to the recessed state, and the region B, in which the cover sheet 12b is bulged out toward the outer side of the container main body 12a to the projecting state, are alternately repeated. In the sterilizing step as well, the states of the region A and the region B appear when the high pressure steam is introduced. Furthermore, in the cooling step, the high pressure steam is not introduced, but the lowering speed of the inner pressure in the autoclave 10 is faster than the lowering speed of the inner pressure of the housing container 12, and thus the situation of the region B arises.

Figure 4:
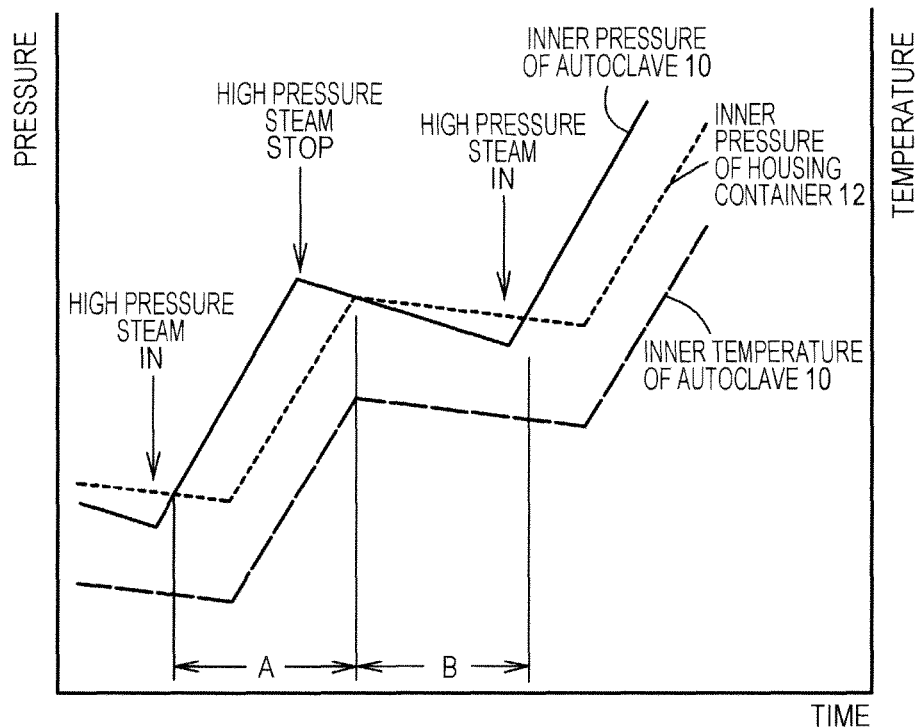
FIG. 4 is a graph showing a temporal change in pressure and temperature in an autoclave and an inner pressure in the housing container when only a high pressure steam is introduced into the autoclave in a temperature-increasing step in a sterilization method for medical instruments, to which the present invention cannot be applied.
Figure 4:
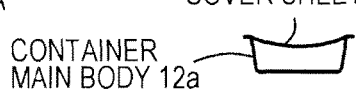
Figure 4:
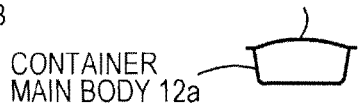

Thus, to prevent the state in which the inner pressure of the autoclave 10 becomes lower than the inner pressure of the housing container 12, the pressure control unit 32b is arranged in the sterilization control device 32 shown in FIG. 1. The pressure control unit 32b appropriately introduces the compressed gas into the autoclave 10 under the steam atmosphere and maintains the current pressure in the autoclave 10 to higher than or equal to the pressure in the housing container 12 through all the steps of the temperature-increasing step, the sterilizing step, and the cooling step. As shown in FIG. 4, the temporal pattern of the inner temperature of the autoclave 10 is similar to the temporal pattern of the inner pressure of the housing container 12. That is, the inner pressure of the housing container 12 becomes close to the saturated steam pressure corresponding to the inner temperature of the autoclave. Thus, in the pressure control unit 32b shown in FIG. 1, the control is carried out with the inner pressure of the housing container 12 replaceable with the saturated steam pressure corresponding to the inner temperature of the autoclave 10. Air, or inactive gas such as nitrogen gas, argon gas, and the like can be as the compressed gas to be introduced into the autoclave 10. Among them, the air is preferred so that a device (not shown) for generating gas, and the like can be omitted, and the sterilizing device can be simplified.

Figure 5:
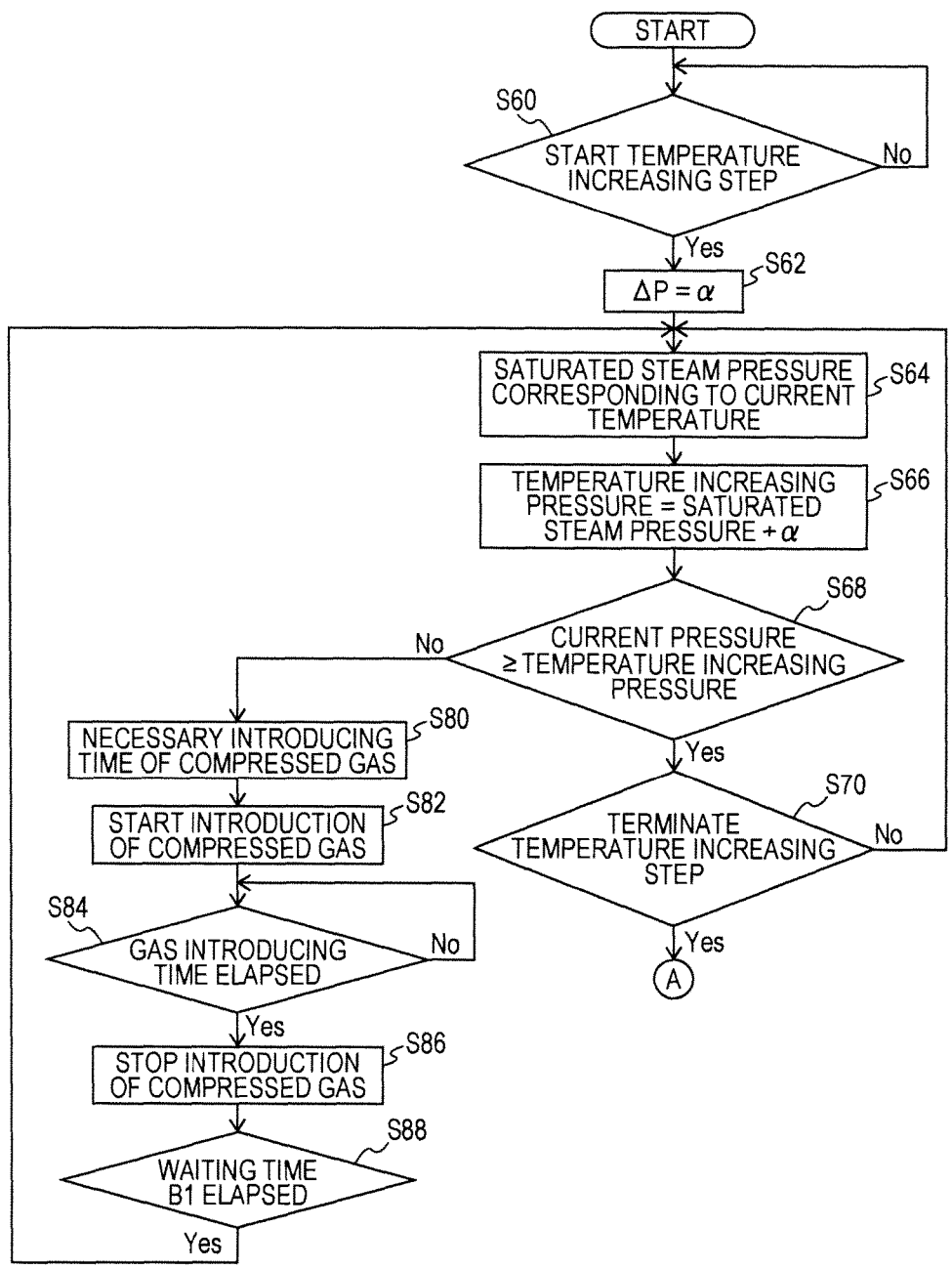
FIG. 5 is a flowchart of the temperature-increasing step of a pressure control unit of the sterilizing device shown in FIG. 1.
Figure 6:
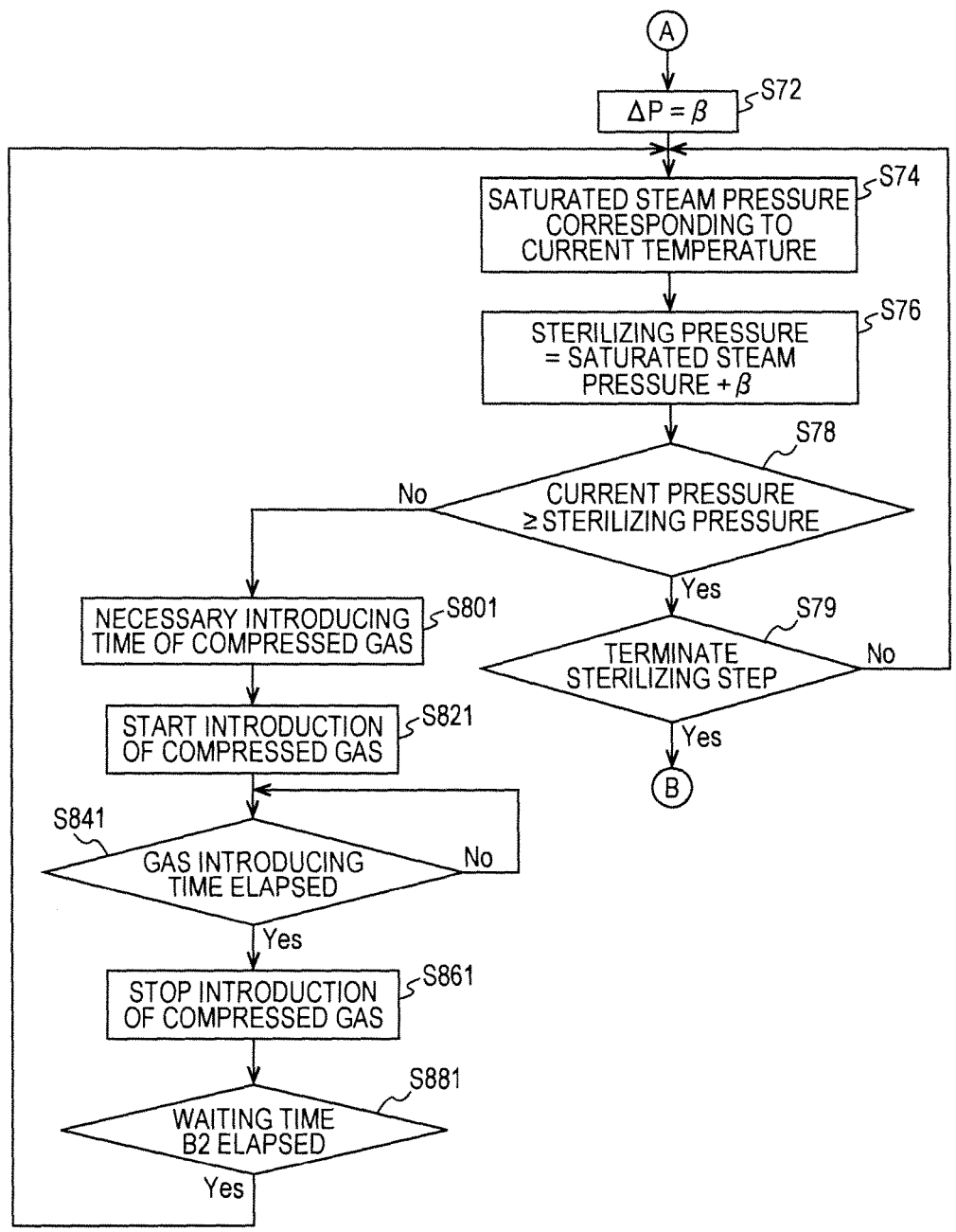
FIG. 6 is a flowchart of a sterilizing step of the pressure control unit of the sterilizing device shown in FIG. 1.
Figure 7:
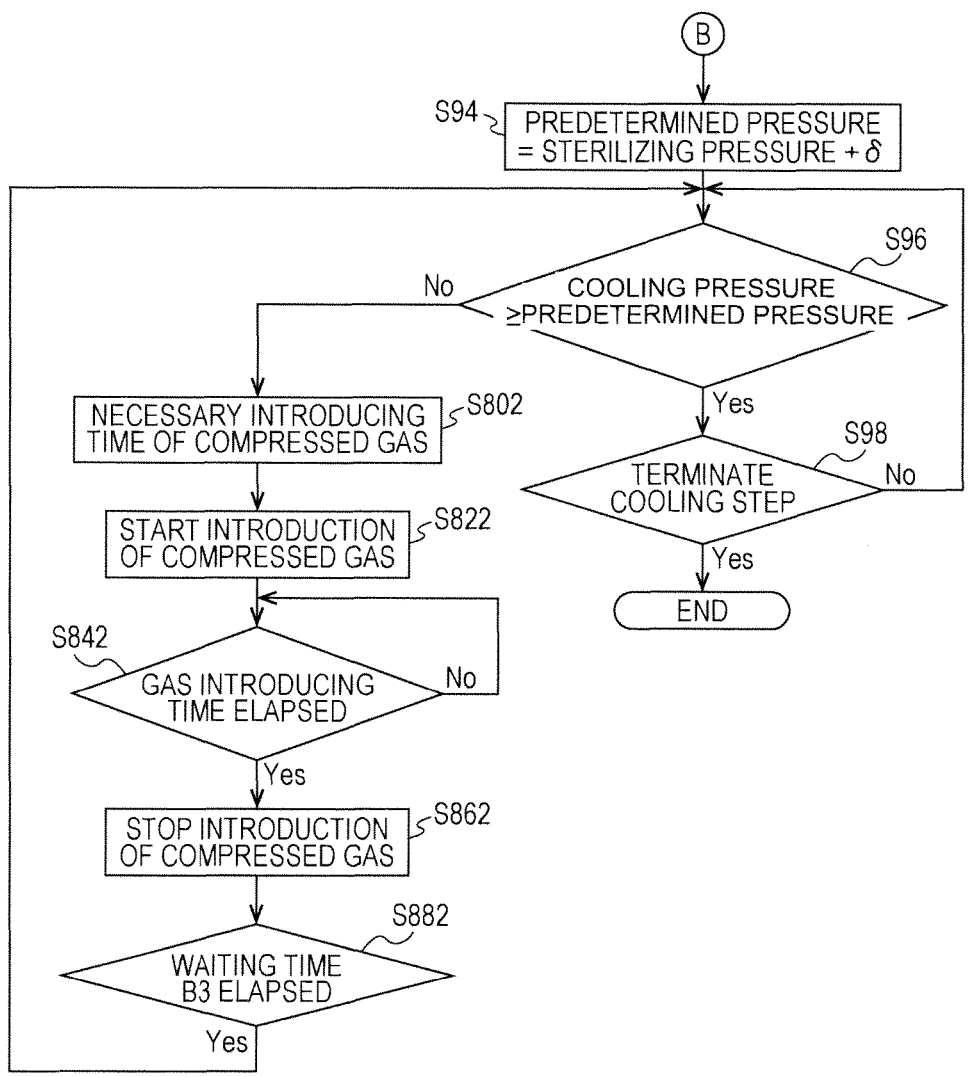
FIG. 7 is a flowchart of a cooling step of the pressure control unit of the sterilizing device shown in FIG. 1.

The flowchart of the pressure control unit 32b is shown in FIGS. 5 to 7. As shown in FIG. 5, when the switch of the sterilizing device is turned ON, the control of the pressure control unit 32b is started, and whether the temperature-increasing step in step S16 (FIG. 3) is started is determined in step S60. If the temperature-increasing step is started, a pressure value ΔP to be added to the saturated steam pressure (substantially corresponds to the inner pressure of the housing container 12) with respect to the current temperature in the autoclave 10 in step S66, to be described later, is assumed as a set in advance in step S62. a is preferably set between 0 to 90 kPa. Next, in step S64, the saturated steam pressure corresponding to the current temperature in the autoclave 10 measured with the temperature sensor 28 is obtained from a table of temperatures and saturated steam pressures stored in advance or is obtained by conversion.

Next, a temperature-increasing pressure, which is the comparative pressure in the temperature-increasing step, is calculated in step S66. The temperature-increasing pressure is obtained by adding the pressure value ΔP (=α) set in advance in S62 to the saturated steam pressure (substantially corresponds to the inner pressure of the housing container 12) corresponding to the current temperature obtained in step S64. The temperature-increasing pressure and the current pressure in the autoclave 10 measured with the pressure sensor 30 are compared in step S68. If the current pressure is higher than or equal to the temperature-increasing pressure, whether the temperature-increasing step in step S28 of the flowchart shown in FIG. 3 is terminated is determined in step S70.

If the current pressure is lower than the temperature-increasing pressure in step S68, the process proceeds to steps S80 to S88 serving as a pressure adjusting means for introducing the compressed gas into the autoclave 10. The necessary introducing time of the compressed gas is calculated from the pressure difference of the current pressure and the temperature-increasing pressure in step S80, and the gas introducing control valve 20 is opened to introduce the compressed gas into the autoclave 10 in step S82 to increase the pressure in the autoclave 10. In this case, the counting of the gas introducing time is started. If the gas introducing time calculated in step S80 has elapsed in step S84, the gas introducing control valve 20 is closed to stop the introduction of the compressed gas in step S86, and the counting of a waiting time B1 is started. The waiting time B1 is provided to actually measure the current temperature and the current pressure in the autoclave 10 for every prescribed time, that is, for intermittently carrying out the pressure adjustment of the autoclave 10, and is preferably five to ten seconds. The degradation of the gas introducing control valve 20 that occurs by frequently repeating the introduction of the compressed gas thus can be prevented.

If the waiting time B1 has elapsed in step S88, the process returns to step 64, and the saturated steam pressure (substantially corresponds to the inner pressure of the housing container 12) corresponding to the current temperature in the autoclave 10 measured with the temperature sensor 28 is again obtained. Next, in step S66, the temperature-increasing pressure in which the pressure value ΔP (=α) set in advance in step S62 is added to the saturated steam pressure (substantially corresponds to the inner pressure of the housing container 12) corresponding to the current temperature obtained in step S64 is calculated. Furthermore, in step S68, whether the current pressure in the autoclave 10 re-measured with the pressure sensor 30 is higher than or equal to the temperature-increasing pressure is determined. If the current pressure is smaller than the temperature-increasing pressure obtained again, the process returns to step S80, and the compressed gas is again introduced to again increase the pressure in the autoclave 10. The pressure-increasing speed in the autoclave 10 by the introduction of the compressed gas is preferably adjusted to 2 to 15 kPa/sec. Thus, an excessive pressure is prevented from being instantaneously applied on the cover sheet 12b thus preventing the cover sheet 12b from being ripped or from being excessively recessed toward the inner side of the container main body 12a and peeling from the opening edge of the container main body 12a.

If the current pressure is higher than or equal to the temperature-increasing pressure obtained again in step S68, it is determined in step S70 whether or not the temperature-increasing step is terminated in step S28 (FIG. 3). If it is determined in step S70 that the temperature-increasing step is not terminated, the process returns to step S64. If it is determined in step S70 that the temperature-increasing step is terminated, the sterilizing step is started in step S30 (FIG. 3). As shown in FIG. 6, in the control flow of the pressure control unit 32b during the sterilizing step, step S72, step S74, step S76, step S78, step S801, step S821, step S841, step S861, and step S881 each correspond to step S62, step S64, step S66, step S68, step S80, step S82, step S84, step S86, and step S88 respectively, similar to the control flow during the temperature-increasing step shown in FIG. 5.

In step S72, the pressure value ΔP to be added to the saturated steam pressure (substantially corresponds to inner pressure of the housing container 12) with respect to the current temperature in the autoclave 10 in step S76 is assumed as β set in advance. β is preferably set to 0 to 90 kPa, and may be the same value as α. Next, in step S74, the saturated steam pressure corresponding to the current temperature in the autoclave 10 measured with the temperature sensor 28 is obtained from a table of temperatures and saturated steam pressures stored in advance, or obtained by conversion. Moreover, in step S76, the sterilizing pressure, in which the pressure value ΔP (=β) set in advance in S72 is added to the saturated steam pressure (substantially corresponds to inner pressure of housing container 12) corresponding to the current temperature obtained in step 74, is calculated with respect to the current pressure measured with the pressure sensor 30 of the autoclave 10. The sterilizing pressure is the comparative pressure in the sterilizing step. In step S78, whether the current pressure in the autoclave 10 measured with the pressure sensor 30 is higher than or equal to the sterilizing pressure calculated in step S76 is determined.

If the current pressure is lower than the sterilizing pressure in step S78, the process proceeds to steps S801 to S881 serving as the pressure adjusting means for introducing the compressed gas into the autoclave 10. The necessary introducing time of the compressed gas is calculated from the pressure difference of the current pressure and the sterilizing pressure in step S801, and the gas introducing control valve 20 is opened to introduce the compressed gas into the autoclave 10 in step S821 to increase the pressure in the autoclave 10. In step S861, when the gas introducing time, for which counting is started in step S801, has elapsed, the gas introducing control valve 20 is closed to stop the introduction of the compressed gas, and the counting of a waiting time B2 is started. The waiting time B2 is preferably five to ten seconds, and may be the same time as the waiting time B1. The pressure-increasing speed in the autoclave 10 by the introduction of the compressed gas is preferably adjusted to 2 to 15 kPa/sec.

After the waiting time B2 has elapsed in step S881, the process returns to step 74, and the steps of S76 to S78 are sequentially executed. If the current pressure is higher than or equal to the sterilizing pressure in step S78, it is determined in step S79 whether or not the sterilizing step is terminated in step S36 (FIG. 3). If it is determined in step S79 that the sterilizing step is not terminates, the process returns to step S74. If it is determined in step S79 that the sterilizing step is terminated, the cooling step is started in step S38 (FIG. 3). The control flow of the pressure control unit 32b during the cooling step is shown in FIG. 7. In the cooling step shown in FIG. 7, the current pressure in the autoclave 10 measured with the pressure sensor 30 and the prescribed pressure are compared in step S96 at substantially the same time as the start of the cooling step. The current pressure corresponds to the cooling pressure. The prescribed pressure is a pressure value calculated in step 94, and is a pressure value obtained by adding δ to the sterilizing pressure, which is the comparative pressure used in the sterilizing step. δ is a pressure value set in advance, and is preferably at least −10 kPa. If the current pressure is higher than or equal to the prescribed pressure in step S96, whether the cooling step is terminated in step S42 of the flowchart shown in FIG. 3 is determined in step S98.

If the current pressure is lower than the prescribed pressure in step S96, the process proceeds to steps S802 to S882 serving as a pressure adjusting means for introducing the compressed gas into the autoclave 10. In step S802, the necessary introducing time of the compressed gas is calculated from the pressure difference of the current pressure and the prescribed pressure, and in step S822, the gas introducing control valve 20 is opened to introduce the compressed gas into the autoclave 10 and increase the pressure in the autoclave 10. In this case, the counting of the gas introducing time is started. If the gas introducing time has elapsed in step S842, the gas introducing control valve 20 is closed and the introduction of the compressed gas is stopped in step S862, and the counting of a waiting time B3 is started. If the waiting time B3 has elapsed in step S882, the process returns to step S96, and whether the current pressure in the autoclave 10 re-measured with the pressure sensor 30 is higher than or equal to the prescribed pressure is determined. If the current pressure is smaller than the prescribed pressure, the process returns to step S802 to again introduce the compressed gas and re-increase the pressure in the autoclave 10. If the current pressure is higher than or equal to the prescribed pressure in step S96, whether the cooling step is terminated in step S46 (FIG. 3) is determined in step S98, and the process returns to step S96 if the cooling step is not terminated. If the cooling step is terminated in step S98, the control of the pressure control unit 32b is terminated. The pressure-increasing speed in the autoclave 10 by the introduction of the compressed gas is preferably adjusted to 2 to 15 kPa/sec. The waiting time B3 is preferably five to ten seconds, and may be the same time as the waiting time B1.

Figure 8:
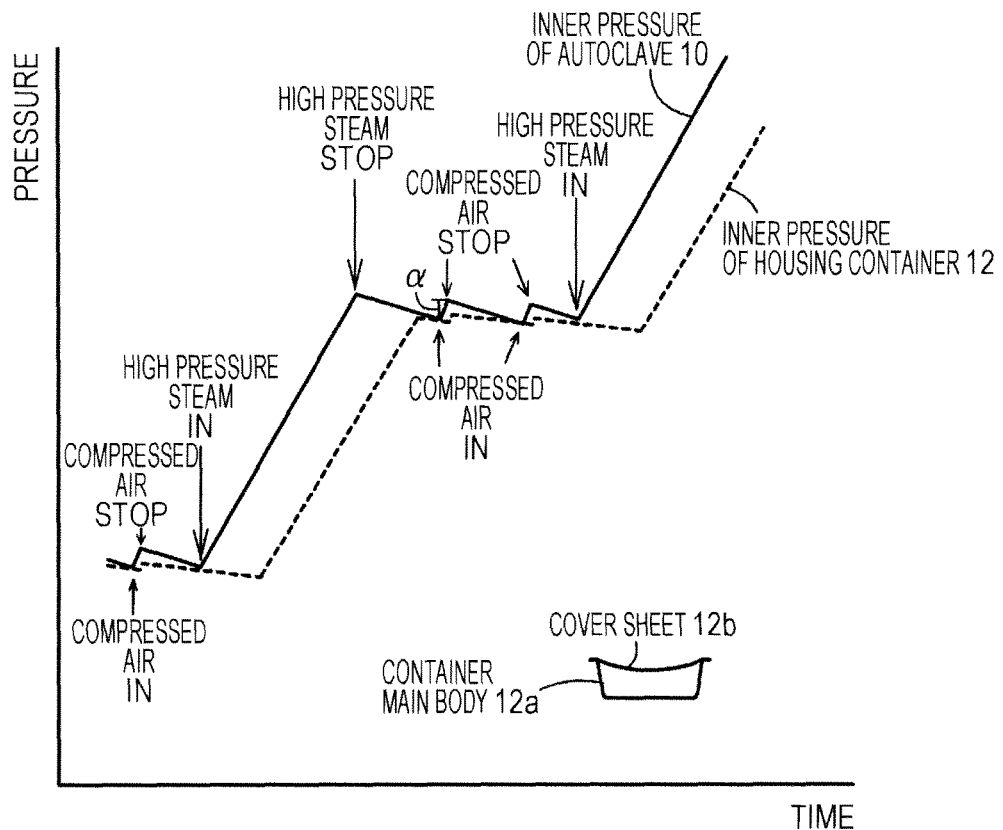
FIG. 8 is a graph showing a temporal change in pressure in the autoclave and an inner pressure in the housing container when the high pressure steam and a compressed gas are introduced into the autoclave in a temperature-increasing step in certain embodiments of the sterilization method for medical instruments, to which the present invention is applied.

According to the control by the flowcharts shown in FIGS. 3, and 5 to 7 of the temperature control unit 32a and the pressure control unit 32b of the sterilization control device 32 shown in FIG. 1, the current pressure in the autoclave 10 is made to be higher than or equal to the saturated steam pressure (substantially corresponds to the inner pressure in the housing container 12) with respect to the current temperature in the autoclave 10 during the temperature-increasing step, the sterilizing step, and the cooling step, so that the cover sheet 12b can be prevented from bulging out toward the outer side of the container main body 12a to the projecting state to the extent that the cover sheet 12b is peeled from the opening edge of the container main body 12a. Thus, even if the heat seal thermoplastic resin 19 attaching the cover sheet 12b to the opening edge of the container main body 12a is heated and softened by the high pressure steam, the cover sheet 12b does not peel from the opening edge of the container main body 12a.

prevention of the cover sheet 12b from bugling out toward the outer side of the container main body 12a to the projecting state to the extent that cover sheet 12b is peeled from the opening edge of the container main body 12a through the temperature-increasing step, the sterilizing step, and the cooling step will be described with a graph showing the temporal change in the pressure in the autoclave 10 and the pressure in the container main body 12a in the temperature-increasing step as shown in FIG. 8. When the introduction of the high pressure steam to the autoclave 10 is started in the temperature-increasing step, the inner pressure of the autoclave 10 immediately rises, but the inner pressure in the housing container 12, which the steam enters from the cover sheet 12b, starts to rise delayed from the rise in the inner pressure of the autoclave 10, similarly to the graph shown in FIG. 4. After the introduction of the high pressure steam is stopped, the steam in the autoclave 10 is heat exchanged with the autoclave 10 main body, the housing container 12, and the like, and then cooled and condensed, whereby the inner pressure in the autoclave 10 immediately lowers. The inner pressure in the housing container 12 rises, but the inner pressure in the autoclave 10 is still higher than the inner pressure of the housing container 12.

The inner pressure of the housing container 12 also starts to lower delayed from the start of lowering of the inner pressure in the autoclave 10, but the lowering speed of the inner pressure in the housing container 12 is slower than the lowering speed of the inner pressure in the autoclave 10, and an event in which the inner pressure of the housing container 12 becomes higher than or equal to the inner pressure of the autoclave 10 may arise. If such event arises, the compressed gas is introduced into the autoclave 10 to increase the pressure so that the current pressure in the autoclave 10 becomes higher than the saturated steam pressure (substantially corresponds to the inner pressure of the housing container 12) corresponding to the current temperature in the autoclave 10 by α. In this case, the pressure in the housing container 12 becomes slightly high, but the current pressure in the autoclave 10 can be made to be higher than or equal to the pressure in the housing container 12. If an event in which the inner pressure of the housing container 12 is higher than or equal to the inner pressure of the autoclave 10 again arises, the compressed gas is again introduced into the autoclave 10. Thus, the current pressure in the autoclave 10 can be always made to be higher than or equal to the pressure in the housing container 12, and the cover sheet 12b can be prevented from bulging out toward the outer side of the container main body 12a to the projecting state.

As shown in FIG. 4, the event in which the inner pressure of the housing container 12 becomes higher than or equal to the inner pressure of the autoclave 10 also arises in the sterilizing step and the cooling step. In the sterilizing step as well, the compressed gas is introduced into the autoclave 10 to increase the pressure so that the current pressure in the autoclave 10 becomes higher than the saturated steam pressure (substantially corresponds to the inner pressure of the housing container 12) corresponding to the current temperature in the autoclave 10 by β, so that the current pressure in the autoclave 10 can be made to be higher than or equal to the pressure in the housing container 12. In the cooling step as well, the current pressure in the autoclave 10 is intermittently pressure-increased to at least a prescribed pressure set in advance to a pressure ($\delta=-10$ kPa) 10 kPa lower than the sterilizing pressure, which is the comparative pressure in the sterilizing step, so that the current pressure in the autoclave 10 can be substantially maintained to higher than or equal to the pressure in the housing container 12. As a result, the housing container 12 terminated with the sterilization and taken out from the autoclave 10 does not have the cover sheet 12b peeled from the opening edge of the container main body 12a and can be provided for transportation to the factory for filling the housed syringe barrel 17 with medical solution in the sterilized state sealed with the cover sheet 12b. In the housing container 12 transported to the medical solution factory, the cover sheet 12b is peeled from the container main body 12a, and the medical solution is filled into the syringe barrel 17 in the clean room.

The inner pressure of the housing container 12 at the start of the cooling step is substantially equal to the inner pressure in the autoclave in the cooling step. The housing container 12 made of plastic is difficult to cool compared to the autoclave 10 made of metal, and thus the steam in the housing container 12 is difficult to condense, and the lowering speed of the inner pressure in the housing container 12 becomes slower than the lowering speed of the inner pressure in the autoclave 10. Furthermore, the higher the temperature, the more rapidly the saturated steam pressure rises. Thus, if the compressed gas is not introduced in the cooling step, the inner pressure of the housing container 12 rises more rapidly than the inner pressure in the autoclave and the cover sheet 12b peels from the opening edge of the container main body 12a when the autoclave is at high temperature, in particular, at the start of cooling.

In this regard, according to the control by the flowchart shown in FIGS. 5 to 7 of the pressure control unit 32b, the current pressure in the autoclave 10 can be pressure-increased to at least the prescribed pressure set in advance to the pressure lower than the sterilizing pressure, which is the comparative pressure in the sterilizing step, by 10 kPa at substantially the same time as the start of the cooling step. Thus, in the cooling step, the inner pressure of the housing container 12 is prevented from rising more rapidly than the inner pressure in the autoclave, and the cover sheet 12b is prevented from peeling from the opening edge of the container main body 12a at the time of high temperature, and in particular, at the start of cooling. The prescribed pressure is preferably a pressure ($\delta>0$ kPa) higher than the sterilizing pressure, which is the comparative pressure in the sterilizing step, and is more preferably the pressure ($\delta=10$ kPa) higher than the sterilizing pressure, which is the comparative pressure in the sterilizing step, by 10 kPa. In the cooling step, the inner pressure of the housing container 12 can be reliably prevented from rising more rapidly than the inner pressure in the autoclave and the cover sheet 12b from peeling from the opening edge of the container main body 12a at the time of high temperature, and in particular, at the start of cooling.

The waiting times B1, B2, and B3 exist in the temperature-increasing step, the sterilizing step, and the cooling step after the introduction of the compressed gas into the autoclave 10 until the comparison of the current pressure in the autoclave 10 with the saturated steam pressure (substantially corresponds to the inner pressure of the housing container 12) corresponding to the current temperature in the autoclave 10 or the prescribed pressure. Thus, a time in which the inner pressure of the housing container 12 becomes greater than or equal to the inner pressure of the autoclave 10 may exist. With each waiting time B1, B2, and B3 set to five to ten seconds, even if the inner pressure of the housing container 12 becomes greater than or equal to the inner pressure of the autoclave 10, the cover sheet 12b can be reliably prevented from bulging out toward the outer side of the container main body 12a to the projecting state to the extent that the cover sheet 12b is peeled from the opening edge of the container main body 12a.

Furthermore, if the temperature sensor is arranged near the bottom portion in the autoclave, the current temperature in the autoclave to be measured tends to be slightly lower than the temperature near the upper portion of the autoclave 10. Thus, the saturated steam pressure corresponding to the current temperature in the autoclave also tends to be slightly lower than the inner pressure of the housing container near the upper portion of the autoclave 10. α and β, which are the pressure value ΔP to be added to the saturated steam pressure (substantially corresponds to the inner pressure of the housing container 12) with respect to the current temperature in the autoclave 10, are preferably 20 kPa to 90 kPa. Accordingly, in each of the temperature-increasing step and the sterilizing step, the inner pressure of the housing container 12 can be reliably prevented from becoming higher than or equal to the inner pressure of the autoclave 10, and the cover sheet 12b can be prevented from bulging out toward the outer side of the container main body 12a to the projecting state to the extent that the cover sheet 12b is peeled from the opening edge of the container main body 12a.

As described above, the pressure adjustment of the interior of the autoclave 10 by the introduction of the compressed gas is carried out in the temperature-increasing step, the sterilizing step, and the cooling step. Thus, in all the steps, the cover sheet 12b can be prevented from bulging out toward the outer side of the container main body 12a to the projecting state.

In the temperature-increasing step, the high pressure steam is intermittently introduced into the autoclave 10, but may be continuously introduced into the autoclave 10. The high pressure steam introducing control valve 14 is controlled by the opening time, but may be opened/closed based on the temperature so as to be opened when the temperature in the autoclave 10 becomes a lower limit value and closed when the temperature becomes an upper limit value. The gas introducing control valve 20 is controlled by the opening time, but may be opened/closed based on the pressure so as to be opened when the pressure in the autoclave 10 becomes a lower limit value and closed when the pressure becomes an upper limit value.

In the flowcharts shown in FIGS. 3 and 5, the gas introducing control valve 20 is opened to introduce the compressed gas into the autoclave 10 when the current pressure in the autoclave 10 becomes lower than the saturated steam pressure corresponding to the current temperature independently from the control of the high pressure steam introducing control valve 14, but the control of the gas introducing control valve 20 and the control of the high pressure steam introducing control valve 14 may be carried out in combination. For example, the high pressure steam introducing control valve 14 and the gas introducing control valve 20 may be controlled by only time. Specifically, the high pressure steam introducing control valve 14 is opened for a constant time for every prescribed time to insert the high pressure steam into the autoclave, and the gas introducing control valve 20 is opened for a constant time after elapse of a prescribed time from when the high pressure steam introducing control valve 14 is closed to introduce the compressed gas into the autoclave 10. The high pressure steam introducing control valve 14 and the gas introducing control valve 20 may be controlled by the time and the pressure in the autoclave 10. Specifically, the high pressure steam introducing control valve 14 is opened for every prescribed time and then closed after introducing the high pressure steam into the autoclave 10 for a prescribed time, and thereafter, the gas introducing control valve 20 is opened to introduce the compressed gas into the autoclave 10 and the gas introducing control valve 20 is closed when the pressure in the autoclave 10 returns to the pressure of when the high pressure steam introducing control valve 14 is closed the previous time.

Alternatively, the high pressure steam introducing control valve 14 and the gas introducing control valve 20 may be controlled by the time and the temperature in the autoclave 10. Specifically, the high pressure steam introducing control valve 14 is opened for every prescribed time and then closed after introducing the high pressure steam into the autoclave 10 for a prescribed time, and thereafter, the gas introducing control valve 20 is opened to introduce the compressed gas into the autoclave 10, the high pressure steam introducing control valve 14 is opened after elapse of a constant time, and the gas introducing control valve 20 is closed when the temperature in the autoclave 10 started to re-increase or when the temperature returned to the temperature of when the high pressure steam introducing control valve 14 is closed the previous time.

In the flowcharts of the temperature-increasing step and the sterilizing step shown in FIGS. 5 and 6, the pressure value $\Delta P$ to be added to the saturated steam pressure (substantially corresponds to the inner pressure of the housing container 12) with respect to the current temperature in the autoclave 10 is $\alpha$, $\beta$ set in advance in each of the temperature-increasing step and the sterilizing step. The pressure value AP may be a set in advance throughout the temperature-increasing step and the sterilizing step. In this case, the fixed value $\alpha$ is input in advance as the pressure value $\Delta P$ to the pressure control unit 32b, and step S62 and step S72 may be omitted.

Figure 9:
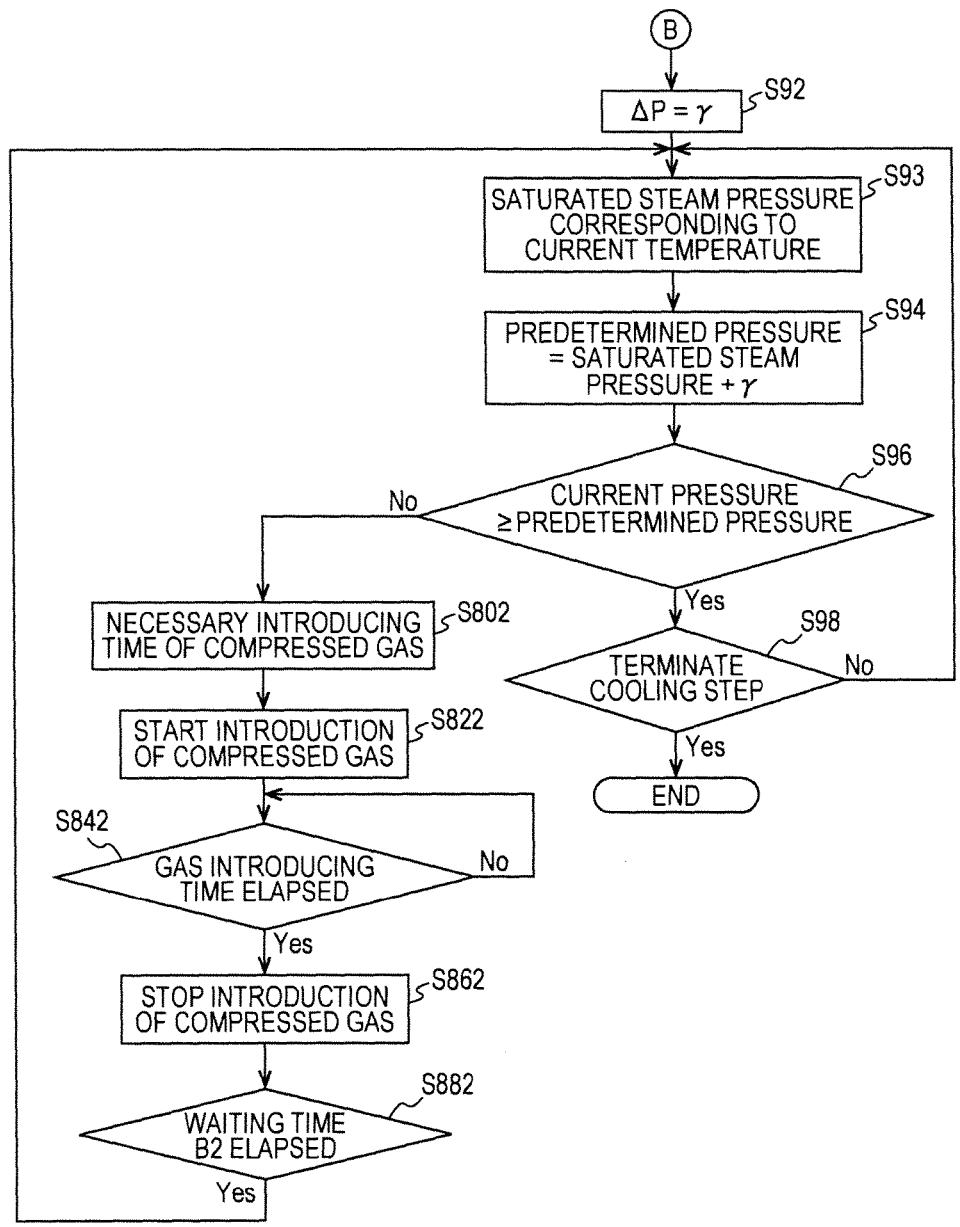
FIG. 9 is another example of a flowchart in a cooling step of the pressure control unit of the sterilizing device shown in FIG. 1.

In the flowchart of the cooling step shown in FIG. 7, the current pressure in the autoclave 10 is intermittently increased to at least the prescribed pressure set in advance to the pressure lower than the sterilizing pressure, which is the comparative pressure in the sterilizing step, by 10 kPa in the cooling step to substantially maintain the current pressure in the autoclave 10 to higher than or equal to the pressure in the housing container 12, but the current pressure in the autoclave may be controlled using the saturated steam pressure with respect to the current temperature in the autoclave 10, similarly to the temperature-increasing step and the sterilizing step. The flowchart for controlling the cooling step using the saturated steam pressure is shown in FIG. 9.

The flowchart shown in FIG. 9 will be described mainly with respect to the portion different from the flowchart shown in FIG. 7. In the flowchart shown in FIG. 9, the pressure value $\Delta P$ to be added to the saturated steam pressure (substantially corresponds to the inner pressure of the housing container 12) with respect to the current temperature in the autoclave 10 in step S94, to be described later, is assumed as $\gamma$ set in advance in step S92. $\gamma$ is preferably 20 kPa to 90 kPa. Next, in step S93, the saturated steam pressure corresponding to the current temperature in the autoclave 10 measured with the temperature sensor 28 is obtained from a table of temperatures and saturated steam pressures stored in advance, or obtained by conversion. The prescribed pressure is then calculated in step S94. The prescribed pressure is obtained by adding the pressure value $\Delta P$ (=$\gamma$) set in advance in S92 to the saturated steam pressure (substantially corresponds to the inner pressure of the housing container 12) corresponding to the current temperature obtained in step S94. The prescribed pressure and the current pressure in the autoclave 10 measured with the pressure sensor 30 are compared in step S96. If the current pressure is greater than or equal to the prescribed pressure, whether the temperature-increasing step is terminated in step S42 of the flowchart shown in FIG. 3 is determined in step S98. If the current pressure is lower than the prescribed pressure in step S96, the process proceeds to steps S802 to S882 serving as a pressure adjusting means for introducing the compressed gas into the autoclave 10. If determined in step S882 that the waiting time B3 has elapsed, the process returns to step S93.

The syringe barrel 17 is housed in a perpendicular state in the housing container 12 shown in FIG. 1, but the syringe barrel 17 may be housed sideways, or other medical instruments such as vial that can be filled with medical solution, surgical knife, forceps, gauze, and the like may be housed in place of the syringe barrel 17.

EXAMPLES

Examples for applying certain embodiments of the present invention will be described in detail below.

First Example

As shown in FIGS. 2(A) and 2(B), a plurality of syringe barrels 17 to be filled with drugs and including a needle at a distal end, a cap that covers the needle, and a flange at a proximal end is housed in a container main body 12a made of plastic in a perpendicular state, and then TYVEK (registered trademark) made from DuPont Co. serving as the cover sheet 12b is thermally bonded to the opening edge of the container main body with the heat seal thermoplastic resin 19 to obtain the housing container 12. The housing container 12 is housed in the autoclave 10, as shown in FIG. 1, and thereafter, the sterilizing process is performed on the syringe barrel 17 in the order of the pressure-reducing step, the temperature-increasing step, the sterilizing step, the cooling step, and the pressure-reducing step of reducing the pressure to atmosphere pressure.

In the pressure-reducing step, the vacuum pump is driven and the pressure-reducing control valve 24 is opened to have the interior of the autoclave 10 in the pressure-reduced state. In this case, the pressure-reducing speed in the autoclave 10 is adjusted to become 30 kPa/min. with the pressure-reducing control valve 24.

In the temperature-increasing step, the high pressure steam introducing control valve 14 is opened at an interval of five to ten seconds and the high pressure steam of pressure 230 kPa is introduced at a temperature 121° C. into the autoclave 10 in the pressure-reduced state obtained in the pressure-reducing step. The introduction of the high pressure steam is continued until the interior of the autoclave 10 reaches the pressure 230 kPa at the temperature 121° C. In the temperature-increasing step, when the current pressure in the autoclave 10 measured with the pressure sensor 30 at an interval of five to ten seconds becomes lower than the pressure in which 20 kPa is added to the saturated steam pressure corresponding to the current temperature in the autoclave 10 measured with the temperature sensor 28, the gas introducing control valve 20 is opened to introduce the compressed air (compressed gas) that passed through the filter 18 into the autoclave 10. The pressure-increasing speed in this case is adjusted to 2 kPa/sec.

In the sterilizing step, the interior of the autoclave 10 is maintained at temperature 121° C. and pressure 230 kPa for 30 minutes. In the sterilizing step as well, when the current pressure in the autoclave 10 measured with the pressure sensor 30 at an interval of five to ten seconds becomes lower than the pressure in which 20 kPa is added to the saturated steam pressure corresponding to the current temperature in the autoclave 10 measured with the temperature sensor 28, the gas introducing control valve 20 is opened to introduce the compressed air (compressed gas) that passed through the filter 18 into the autoclave 10 for the necessary introducing time. The pressure-increasing speed in this case is adjusted to 2 kPa/sec.

In the cooling step, the inner temperature is lowered by heat release from the autoclave 10. The cooling speed is 10° C./min. In the cooling step as well, when the current pressure in the autoclave 10 measured with the pressure sensor 30 at an interval of five to ten seconds becomes lower than the pressure in which 20 kPa is added to the saturated steam pressure corresponding to the current temperature in the autoclave 10 measured with the temperature sensor 28, the gas introducing control valve 20 is opened to introduce the compressed air (compressed gas) that passed through the filter 18 into the autoclave 10 by the necessary introducing time. The pressure-increasing speed in this case is adjusted to 2 kPa/sec.

In the pressure-reducing step of reducing the pressure to atmosphere pressure, when the temperature in the autoclave 10 reaches 50° C. in the cooling step, the release control valve 26 is opened to discharge the steam and the air (compressed gas) in the autoclave 10 to atmosphere to reduce the pressure in the interior of the autoclave 10 to the atmosphere pressure. In this case, the opening degree of the release control valve 26 is adjusted, and the pressure-reducing speed in the autoclave 10 is adjusted to become about 30 kPa/min.

The cover sheet 12b of the housing container 12 taken out from the autoclave 10 in which the pressure is reduced to atmosphere pressure is sufficiently thermally bonded to the opening edge of the container main body 12a through the heat seal thermoplastic resin 19, and the peeled area is not found at all.

First Comparative Example

Compared to the first example, the sterilizing process is performed on the syringe barrel 17 similarly to the first example other than that the pressure is not increased in the autoclave 10 by the introduction of the compressed gas. The cover sheet 12b of the housing container 12 taken out from the autoclave 10 in which the pressure is reduced to the atmosphere pressure is peeled from the opening edge of the container main body 12a in some areas. At the area with the largest peeling, a peeling length/width is about 5 mm.

Second Comparative Example

Compared to the first example, when increasing the temperature in the autoclave 10 in the temperature-increasing step, sterilization is performed similarly to the first example other than that the time for opening the high pressure steam introducing control valve 14 is calculated with the temperature control unit 28 so that a target value and the actually measured temperature of the temperature sensor 28 match from a difference of the target value and the actually measured temperature measured with the temperature sensor 28, and then the high pressure steam is introduced into the autoclave 10. The cover sheet 12b of the housing container 12 taken out from the autoclave 10 in which the pressure is reduced to atmosphere pressure is sufficiently thermally bonded to the opening edge of the container main body 12a through the heat seal thermoplastic resin 19, and the peeled area is not found at all.

Third Comparative Example

Compared to the first example, the sterilizing process is performed on the syringe barrel 17 similarly to the first example, other than that the compressed air (compressed gas) is introduced to continuously maintain the pressure in the autoclave in the cooling step to the sterilizing pressure of 230 kPa (δ=20 kPa) in the sterilizing step. The cover sheet 12b of the housing container 12 taken out from the autoclave 10 in which the pressure is reduced to the atmosphere pressure is sufficiently thermally bonded to the opening edge of the container main body 12a through the heat seal thermoplastic resin 19, and the peeled area is not found at all.

What is claimed is:
1. A sterilization method for a medical instrument, the sterilization method comprising:
    a step of providing a medical instrument housed in a housing container, the housing container including:

a container main body including a bottom portion at a lower end, a peripheral wall portion extending from a periphery of the bottom portion toward an upper end, and an opening surrounded by the upper end of the peripheral wall portion; and a gas permeable and micro-particle impermeable cover sheet that covers and seals the opening, the cover sheet being thermally bonded to the upper end of the peripheral wall portion of the container main body with a heat seal thermoplastic resin to seal the opening;

a step of housing the housing container in an autoclave;

a temperature-increasing step of introducing high pressure steam into the autoclave to increase a temperature within the autoclave to a prescribed temperature;

a sterilizing step of holding the temperature within the autoclave at the prescribed temperature for a prescribed time to sterilize the medical instrument; and a cooling step of reducing the temperature within the autoclave, wherein, in the temperature-increasing step, the sterilizing step, and the cooling step, compressed gas is introduced into the autoclave under a steam atmosphere obtained by the introduction of the high pressure steam to increase a current pressure in the autoclave to higher than or equal to a pressure in the housing container and inhibit the cover sheet from peeling from the upper end of the peripheral wall portion, wherein, in the temperature-increasing step, when the current pressure in the autoclave becomes lower than a temperature-increasing pressure, the temperature-increasing pressure being a pressure obtained by adding a first preset pressure value to a saturated steam pressure corresponding to a current temperature in the autoclave, the compressed gas is introduced to increase the current pressure in the autoclave to higher than or equal to the temperature-increasing pressure, and wherein, in the sterilizing step, when the current pressure in the autoclave becomes lower than a sterilizing pressure, the sterilizing pressure being a pressure obtained by adding a second preset pressure value to a saturated steam pressure corresponding to a current temperature in the autoclave, the compressed gas is introduced to increase the current pressure in the autoclave to higher than or equal to the sterilizing pressure.

2. The sterilization method for the medical instrument according to claim 1, wherein, in the temperature-increasing step, a current temperature and the current pressure in the autoclave are actually measured at predetermined time intervals, and when the actually measured current pressure in the autoclave becomes lower than the temperature-increasing pressure, which is a pressure obtained by adding the first preset pressure value to a saturated steam pressure corresponding to the actually measured current temperature, the compressed gas is introduced into the autoclave to increase the current pressure in the autoclave to higher than or equal to the temperature-increasing pressure, and wherein, in the sterilizing step, a current temperature and the current pressure in the autoclave are actually measured at predetermined time intervals, and when the actually measured current pressure in the autoclave becomes lower than the sterilizing pressure, which is a pressure obtained by adding the second preset pressure value to a saturated steam pressure corresponding to the actually measured current temperature, the compressed gas is introduced into the autoclave to increase the current pressure in the autoclave to higher than or equal to the sterilizing pressure.

3. The sterilization method for the medical instrument according to claim 2, wherein the current temperature is actually measured with a temperature sensor arranged near a bottom portion in the autoclave, and each of the first preset pressure value and the second preset pressure value is in a range of 20 to 90 kPa.

4. The sterilization method for the medical instrument according to claim 3, wherein, in the cooling step, when the current pressure in the autoclave becomes lower than a prescribed pressure that is preset to a pressure higher than the sterilizing pressure, the compressed gas is introduced to increase the current pressure in the autoclave to higher than or equal to the prescribed pressure.

5. The sterilization method for the medical instrument according to claim 4, further comprising, before the temperature-increasing step, a pressure-reducing step of reducing a pressure of an interior of the autoclave to lower than an atmospheric pressure, wherein a pressure-reducing speed in the autoclave in the pressure-reducing step is adjusted to be within a range of 5 to 40 kPa/min.

6. The sterilization method for the medical instrument according to claim 5, wherein, in the cooling step, when a current temperature in the autoclave becomes lower than or equal to 60° C., the cooling step is terminated, and a remaining pressure in the autoclave is released to an outside atmosphere such that an interior of the autoclave is at an atmospheric pressure.

7. The sterilization method for the medical instrument according to claim 6, wherein the medical instrument is a syringe barrel configured to be filled with a drug and including a needle at a distal end, a cap that covers the needle, and a flange at a proximal end, and wherein the housing container further includes a shelf arranged on the peripheral wall portion, a nested plate that is arranged on the shelf, and a plurality of tubular receiving cylinders arranged on the nested plate, wherein each of the tubular receiving cylinders is configured such that the syringe barrel is removably insertable therein and hangable thereon by the flange of the syringe barrel.

8. The sterilization method for the medical instrument according to claim 1, wherein, in the cooling step, when the current pressure in the autoclave becomes lower than a prescribed pressure that is preset to a pressure higher than the sterilizing pressure, the compressed gas is introduced to increase the current pressure in the autoclave to higher than or equal to the prescribed pressure.

9. The sterilization method for the medical instrument according to claim 1, wherein, in the temperature-increasing step, the high pressure steam is intermittently introduced into the autoclave.

10. The sterilization method for the medical instrument according to claim 1, further comprising, before the temperature-increasing step, a pressure-reducing step of reducing a pressure of an interior of the autoclave to lower than an atmospheric pressure, wherein a pressure-reducing speed in the autoclave in the pressure-reducing step is adjusted to be within a range of 5 to 40 kPa/min.

11. The sterilization method for the medical instrument according to claim 1, wherein, in the cooling step, when a current temperature in the autoclave becomes lower than or equal to 60° C., the cooling step is terminated, and a remaining pressure in the autoclave is released to an outside atmosphere such that an interior of the autoclave is at an atmospheric pressure.

12. The sterilization method for the medical instrument according to claim 1,
wherein the medical instrument is a syringe barrel configured to be filled with a drug and including a needle at a distal end, a cap that covers the needle, and a flange at a proximal end, and
wherein the housing container further includes a shelf arranged on the peripheral wall portion, a nested plate that is arranged on the shelf, and a plurality of tubular receiving cylinders arranged on the nested plate,
wherein each of the tubular receiving cylinders is configured such that the syringe barrel is removably insertable therein and hangable thereon by the flange of the syringe barrel.

13. A sterilization method for a medical instrument, the sterilization method comprising:
a step of providing a medical instrument housed in a housing container, the housing container including:
a container main body including a bottom portion at a lower end, a peripheral wall portion extending from a periphery of the bottom portion toward an upper end, and an opening surrounded by the upper end of the peripheral wall portion; and
a gas permeable and micro-particle impermeable cover sheet that covers and seals the opening, the cover sheet being thermally bonded to the upper end of the peripheral wall portion of the container main body with a heat seal thermoplastic resin to seal the opening;
a step of housing the housing container in an autoclave;
a pressure-reducing step of reducing a pressure of an interior of the autoclave to lower than an atmospheric pressure, wherein a pressure-reducing speed in the autoclave in the pressure-reducing step is adjusted to be within a range of 5 to 40 kPa/min;
a temperature-increasing step of introducing high pressure steam into the autoclave to increase a temperature within the autoclave to a prescribed temperature;
a sterilizing step of holding the temperature within the autoclave at the prescribed temperature for a prescribed time to sterilize the medical instrument; and
a cooling step of reducing the temperature within the autoclave,
wherein, in the temperature-increasing step, the sterilizing step, and the cooling step, compressed gas is introduced into the autoclave under a steam atmosphere obtained by the introduction of the high pressure steam to increase a current pressure in the autoclave to higher than or equal to a pressure in the housing container and inhibit the cover sheet from peeling from the upper end of the peripheral wall portion.

14. A sterilization method for a medical instrument, the sterilization method comprising:
a step of providing a medical instrument housed in a housing container, the housing container including:
a container main body including a bottom portion at a lower end, a peripheral wall portion extending from a periphery of the bottom portion toward an upper end, and an opening surrounded by the upper end of the peripheral wall portion; and
a gas permeable and micro-particle impermeable cover sheet that covers and seals the opening, the cover sheet being thermally bonded to the upper end of the peripheral wall portion of the container main body with a heat seal thermoplastic resin to seal the opening;
a step of housing the housing container in an autoclave;
a temperature-increasing step of introducing high pressure steam into the autoclave to increase a temperature within the autoclave to a prescribed temperature;
a sterilizing step of holding the temperature within the autoclave at the prescribed temperature for a prescribed time to sterilize the medical instrument; and
a cooling step of reducing the temperature within the autoclave,
wherein, in the temperature-increasing step, the sterilizing step, and the cooling step, compressed gas is introduced into the autoclave under a steam atmosphere obtained by the introduction of the high pressure steam to increase a current pressure in the autoclave to higher than or equal to a pressure in the housing container and inhibit the cover sheet from peeling from the upper end of the peripheral wall portion, and
wherein, in the cooling step, when a current temperature in the autoclave becomes lower than or equal to 60° C., the cooling step is terminated, and a remaining pressure in the autoclave is released to an outside atmosphere such that an interior of the autoclave is at an atmospheric pressure.

* * * * *